United States Patent
Cheung et al.

(10) Patent No.: US 10,109,476 B2
(45) Date of Patent: Oct. 23, 2018

(54) SUBSTRATE PROCESSING METHOD FOR DEPOSITING A BARRIER LAYER TO PREVENT PHOTORESIST POISONING

(71) Applicant: Lam Research Corporation, Fremont, CA (US)

(72) Inventors: David Cheung, Foster City, CA (US); Ilia Kalinovski, Berkeley, CA (US)

(73) Assignee: LAM RESEARCH CORPORATION, Fremont, CA (US)

( * ) Notice: Subject to any disclaimer, the term of this patent is extended or adjusted under 35 U.S.C. 154(b) by 0 days.

(21) Appl. No.: 15/628,739

(22) Filed: Jun. 21, 2017

(65) Prior Publication Data
US 2018/0005819 A1  Jan. 4, 2018

Related U.S. Application Data
(60) Provisional application No. 62/357,619, filed on Jul. 1, 2016.

(51) Int. Cl.
*H01L 21/02* (2006.01)
*H01L 21/3105* (2006.01)
*H01L 21/311* (2006.01)
*C07F 7/10* (2006.01)

(52) U.S. Cl.
CPC .. *H01L 21/02167* (2013.01); *H01L 21/02362* (2013.01); *H01L 21/3105* (2013.01); *H01L 21/31144* (2013.01); *C07F 7/10* (2013.01); *H01L 21/02211* (2013.01); *H01L 21/02219* (2013.01); *H01L 21/02271* (2013.01)

(58) Field of Classification Search
CPC ................................. H01L 21/02362
See application file for complete search history.

(56) References Cited

U.S. PATENT DOCUMENTS

| | | | |
|---|---|---|---|
| 2003/0064607 A1* | 4/2003 | Leu | C23C 16/02 438/780 |
| 2004/0110390 A1* | 6/2004 | Takagi | H01L 27/105 438/710 |

* cited by examiner

*Primary Examiner* — Karen Kusumakar

(57) ABSTRACT

A method for depositing a barrier layer includes a) arranging a substrate including a nitride layer in a processing chamber; b) setting a process temperature in the processing chamber to a predetermined process temperature range; c) setting a process pressure in the processing chamber to a predetermined process pressure range; d) supplying at least one of a gas and a vapor including an organosilane precursor species; and e) depositing a barrier layer on the nitride layer. The barrier layer reduces diffusion of nitrogen-containing groups in the nitride layer into a photoresist layer that is subsequently deposited on the nitride layer.

20 Claims, 4 Drawing Sheets

SUBSTRATE PROCESSING METHOD FOR DEPOSITING A BARRIER LAYER TO PREVENT PHOTORESIST POISONING

CROSS-REFERENCE TO RELATED APPLICATIONS

This application claims the benefit of U.S. Provisional Application No. 62/357,619, filed on Jul. 1, 2016. The entire disclosure of the application referenced above is incorporated herein by reference.

FIELD

The present disclosure relates to substrate processing methods, and more particularly to substrate processing methods for depositing a barrier layer on a nitride layer to prevent poisoning of a photoresist layer.

BACKGROUND

The background description provided here is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Substrate processing systems may be used to deposit, etch or treat film on a substrate such as a semiconductor wafer. The substrate processing systems typically include a processing chamber, a gas distribution device such as a showerhead and a substrate support. During processing, the substrate is arranged on the substrate support. Different gas mixtures may be introduced into the processing chamber and heat or radio frequency (RF) plasma may be used during some processes to activate chemical reactions.

During substrate processing, a photoresist layer may be used to pattern an underlying layer. For example in FIG. 1, a substrate 30 may include a nitride layer 36 such as silicon nitride (SiN) or silicon carbonitride (SiCN) that is deposited on one or more underlying layers 40. A photoresist layer 34 may be deposited on the nitride layer 36 to pattern the nitride layer 36. However, nitrogen-containing groups from the nitride layer 36 may diffuse into the photoresist layer 34 and poison the photoresist layer 34.

In some processes, a thin oxide layer may be formed on the top of the nitride layer 36 to prevent diffusion of the N-containing groups into the photoresist layer 34. The thin oxide layer may be deposited by exposing the nitride layer 36 to oxidizing plasma. However, this approach usually forms the thin oxide layer by consuming nitride. Loss of nitride may not be acceptable in some processes due to more stringent material loss requirements of these processes.

SUMMARY

A method for depositing a barrier layer includes a) arranging a substrate including a nitride layer in a processing chamber; b) setting a process temperature in the processing chamber to a predetermined process temperature range; c) setting a process pressure in the processing chamber to a predetermined process pressure range; d) supplying at least one of a gas and a vapor including an organosilane precursor species; and e) depositing a barrier layer on the nitride layer. The barrier layer reduces diffusion of nitrogen-containing groups in the nitride layer into a photoresist layer that is subsequently deposited on the nitride layer.

In other features, the organosilane species includes one or more $SiCH_3$ functional groups. The organosilane species has a form $R_nSiX_m$, wherein R includes one or more organic functional groups and X includes one or more hydrolysable functional groups that react with —OH or —H active sites on a surface of the substrate. The one or more hydrolysable functional groups are selected from a group consisting of primary amine groups, secondary amine groups, tertiary amine groups, alcoxy groups (—OR), acyloxy groups (—O(CO)R), and halogen atoms.

In other features, the method includes performing plasma pretreatment on the nitride layer before e).

In other features, the method includes performing plasma post-treatment on the barrier layer after e).

In other features, the method includes f) depositing a photoresist layer on the barrier layer. In other features, the method includes performing a plasma post-treatment process on the barrier layer after e) and before f). In other features, the organosilane species bond with SiOH and SiH dangling bonds. In other features, the organosilane species is selected from a group consisting of dimethylaminotrimethylsilane (DMATMS), di(sec-butylamino)silane (DSBAS), and bis(tert-butylamino)silane (BTBAS).

In other features, the predetermined process temperature range is from 200° C. to 400° C. The predetermined process temperature range is from 260° C. to 300° C. The predetermined process pressure range is from 300 mTorr to 5 Torr. The predetermined process pressure range is from 1 Torr to 2 Torr. The barrier layer has a thickness of 5 Å to 100 Å. The barrier layer has a thickness of 10 Å to 20 Å.

In other features, d) further comprises supplying a carrier gas selected from a group consisting of molecular hydrogen, molecular nitrogen, argon, helium, and an inert gas. The nitride layer is selected from a group consisting of silicon nitride and silicon carbonitride.

In other features, performing the plasma pretreatment includes exposing the nitride layer to plasma process gas including hydrogen.

In other features, the hydrogen comprises 4% to 100% of the plasma process gas.

Further areas of applicability of the present disclosure will become apparent from the detailed description, the claims and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings, wherein.

In the drawings, reference numbers may be reused to identify similar and/or identical elements.

DETAILED DESCRIPTION

The present disclosure relates to methods for depositing a barrier layer on a substrate including a nitride layer prior to deposition of a photoresist layer. The barrier layer prevents nitrogen poisoning of the photoresist layer. The barrier layer that is formed is not subtractive for the nitride layer and will help meet material loss requirements of more stringent processes.

In some examples, the barrier layer is formed by modification of the nitride layer by chemical reaction of a surface thereof with a precursor in gas or vapor state. In some examples, the precursor includes an organosilane or a similar class of molecules that is capable of forming stable chemical bonds with a surface of the nitride layer and without consuming nitride.

The barrier layer formed by the reaction is stable, conformal, contiguous, and impermeable to photoresist poisoning species. In some examples, the barrier layer includes a monolayer of interlinked organosilane groups bound to the surface of the nitride layer. Presence of the barrier layer on the surface of the nitride layer is unlikely to create problems during subsequent processing. The organosilane layer is converted into oxide during photoresist ashing or stripping and the oxide is dissolved by a wet clean process. The net result to the nitride layer will be zero loss.

Figure 1:
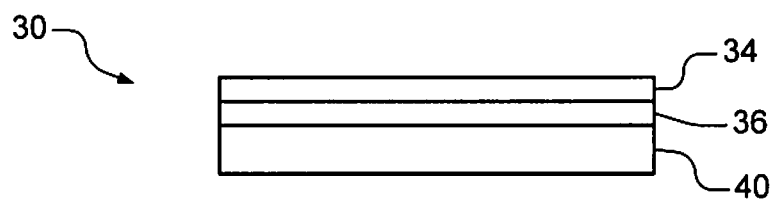
FIG. 1 is a side cross-sectional view of an example of a substrate including a nitride layer and a photoresist layer according to the prior art.
Figure 2:
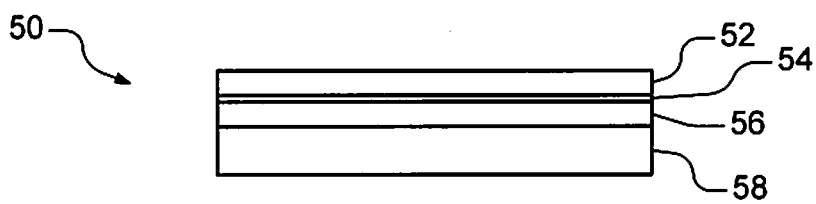
FIG. 2 is a side cross-sectional view of an example of a substrate including a nitride layer and a photoresist layer according to the present disclosure.

Referring now to FIG. 2, a substrate 50 includes a nitride layer 56 deposited on one or more underlying layers 58. A barrier layer 54 is deposited on the nitride layer 56. A photoresist layer 52 is deposited on the barrier layer 54. In some examples, the nitride layer 56 includes silicon nitride (SiN), silicon carbonitride (SiCN) or other nitride film.

Figure 3:
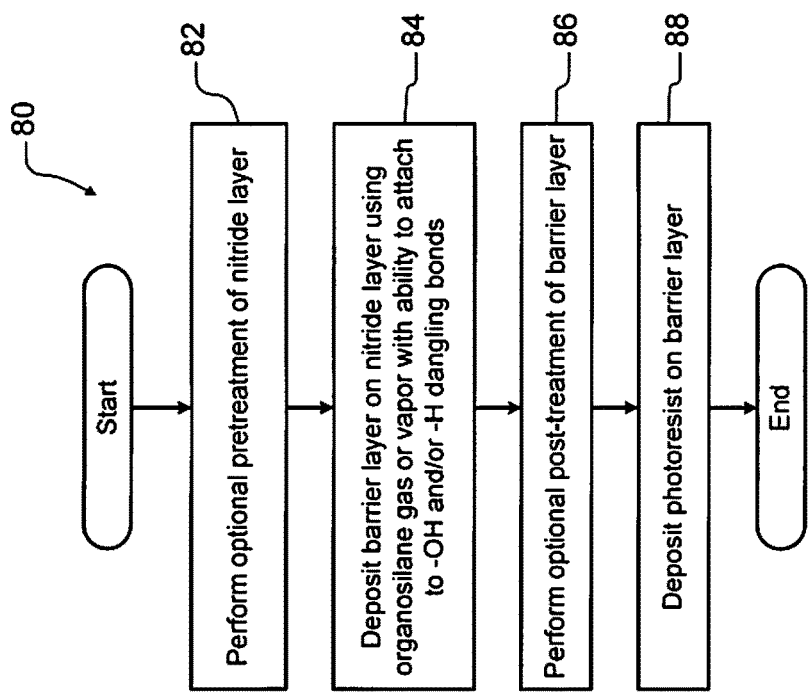
FIG. 3 is a flowchart of an example of a method for depositing a barrier layer according to the present disclosure.

Referring now to FIG. 3, a method 80 for depositing the barrier layer is shown. At 82, optional pretreatment of the nitride layer is performed. After the nitride layer is deposited, a native oxide layer builds up on the nitride layer and creates silicon oxynitride (SiON) at a surface thereof. The bonding layer typically has a difficult time bonding with the SiON. The pretreatment process may be used to create SiOH or SiH dangling bonds that improve bonding with the barrier layer.

At 84, a barrier layer is deposited on the nitride layer. In some examples, the barrier layer is deposited using an organosilane precursor gas. In other examples, the barrier layer is deposited using vapor. The vapor can be supplied by delivering a carrier gas to an ampoule including a liquid organosilane precursor. The ampoule can be heated or unheated. Organosilane precursor vapor is carried by the carrier gas to the processing chamber.

In some examples, the organosilane precursor includes one or more $SiCH_3$ functional groups. In some examples, the organosilane precursor has the ability to attach to SiOH and/or SiH dangling bonds. Organosilane precursors have a general form $R_nSi_iX_m$, where R includes one or more organic functional groups and X includes one or more hydrolysable functional groups that react with —OH or —H active sites on a surface of the substrate. Examples of hydrolysable functional groups include the following: amine groups (primary, secondary or tertiary amines), alcoxy groups (—OR), acyloxy groups (—O(CO)R), or halogen atoms. In some examples, the organosilane precursor includes dimethylaminotrimethylsilane (DMATMS), di(sec-butylamino)silane (DSBAS), and bis(tert-butylamino)silane (BTBAS), although other organosilane precursors may be used.

At 86, optional post-treatment of the barrier layer is performed. At 88, a photoresist layer is deposited on the barrier layer for subsequent patterning of the nitride layer and/or underlying layers. The post-treatment process helps to make the barrier layer compatible with the photoresist layer that is subsequently deposited.

Figure 4:
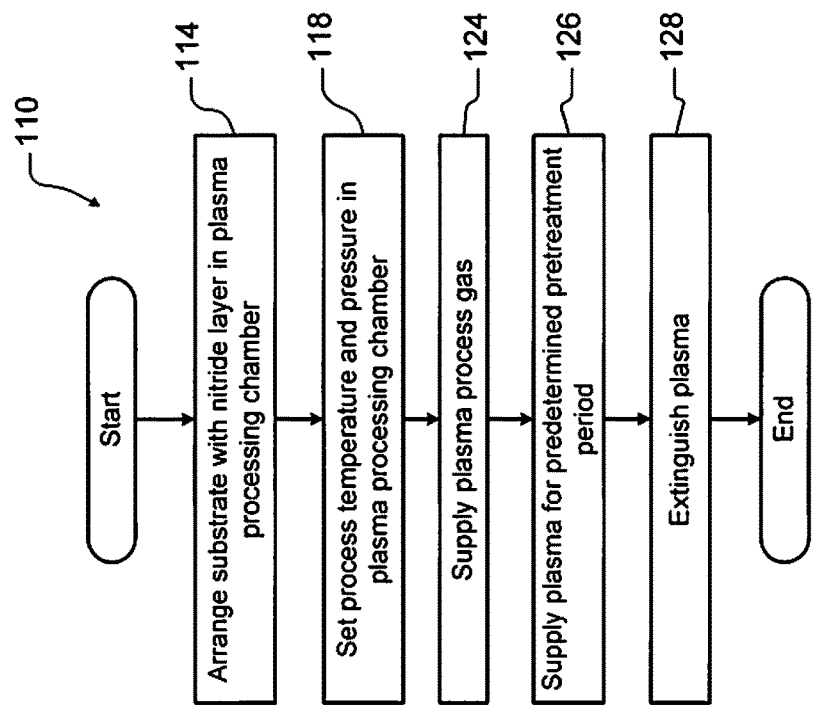
FIG. 4 is a flowchart of an example of a pretreatment method performed prior to deposition of the barrier layer according to the present disclosure.

Referring now to FIG. 4, a pretreatment method 110 may be performed prior to deposition of the barrier layer. At 114, the substrate is arranged in a plasma processing chamber. In some examples, the plasma processing chamber includes a downstream plasma processing chamber. At 118, process temperature and pressure are set to predetermined values in the plasma processing chamber. At 124, plasma process gas is supplied to the processing chamber. At 126, plasma is struck and maintained in the processing chamber for a predetermined pretreatment period. At 128, after the predetermined pretreatment period, the plasma is extinguished.

In some examples, the pretreatment process may employ hydrogen-based plasma, although other plasma process gas may be used. In some examples, the plasma process gas includes forming gas (a mixture of 96% nitrogen and 4% hydrogen gas). In other examples, the plasma process gas includes molecular hydrogen at a concentration between 4% and 100%. In other examples, the plasma process gas includes molecular hydrogen gas (at a concentration between 4% and 100%) and molecular nitrogen and/or helium. In some examples, the plasma process gas is oxygen-free.

In some examples, RF power is in a range from 1 kW to 10 kW. In some examples, the RF power is in a range from 4 kW to 5 kW. In some examples, the RF power is 4.5 KW. In some examples, the flow rate of the plasma process gas is in a range from 1 to 20 liters per minute. In some examples, the flow rate is 8 to 12 liters per minute. In some examples, the flow rate of the plasma process gas is 10 liters per minute. In some examples, the process pressure is in a range from 300 mTorr to 5 Torr. In some examples, the process pressure is in a range from 1 Torr to 2 Torr. In some examples, the process pressure is 1.5 Torr. In some examples, the process temperature is in a range from 200 to 400° C. In some examples, the predetermined pretreatment period is in range from 1 second to 60 seconds.

Figure 5:
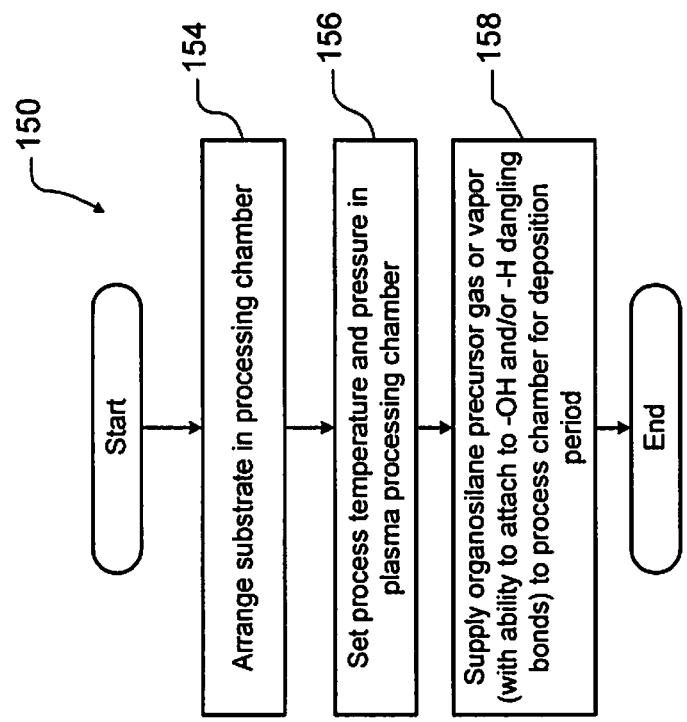
FIG. 5 is a flowchart of an example of a method for depositing the barrier layer according to the present disclosure.

Referring now to FIG. 5, a method 150 for depositing the barrier layer is shown. The barrier layer is deposited thermally without plasma. At 154, the substrate is arranged in a processing chamber. At 156, process temperature and pressure are set to predetermined values in the plasma processing chamber. At 158, process gas or vapor including organosilane species is supplied to the processing chamber. In some examples, a carrier gas such argon (Ar), molecular nitrogen ($N_2$), helium (He), and/or an inert gas is also supplied.

In some examples, the organosilane precursor includes one or more $SiCH_3$ functional groups. In some examples, the organosilane precursor has the ability to attach to SiOH and/or SiH dangling bonds. Organosilane precursors have a general form $R_nSi_iX_m$, where R includes one or more organic functional groups and X includes one or more hydrolysable functional groups that react with —OH or —H active sites on a surface of the substrate. Examples of hydrolysable functional groups include the following: amine groups (primary, secondary or tertiary amines), alcoxy groups (—OR), acyloxy groups (—O(CO)R), or halogen atoms. In some examples, the organosilane precursor includes dimethylaminotrimethylsilane (DMATMS), di(sec-butylamino)silane (DSBAS), and bis(tert-butylamino)silane (BTBAS), although other organosilane precursors may be used.

In some examples, the organosilane precursor gas is supplied at a rate of 0.5 to 10 g per minute. In other examples, the organosilane precursor gas is supplied at a rate of 2 g per minute. The organosilane precursor gas is supplied during a predetermined deposition period.

In some examples, the process pressure is in a range from 300 mTorr to 5 Torr. In some examples, the process pressure is in a range from 1 Torr to 2 Torr. In some examples, the process pressure is 1.5 Torr. In some examples, the process temperature is in a range from 200° C. to 400° C. In some examples, the process temperature is in a range from 260° C. to 300° C. In some examples, the process temperature is 285° C. In some examples, the process period is in range from 30 seconds to 600 seconds. In some examples, the process period is 100 to 140 seconds. In some examples, the process period is 120 seconds. In some examples, the barrier layer is deposited to a thickness of 5 Å to 100 Å. In other examples, the barrier layer is deposited to a thickness of 10 Å to 20 Å.

Figure 6:
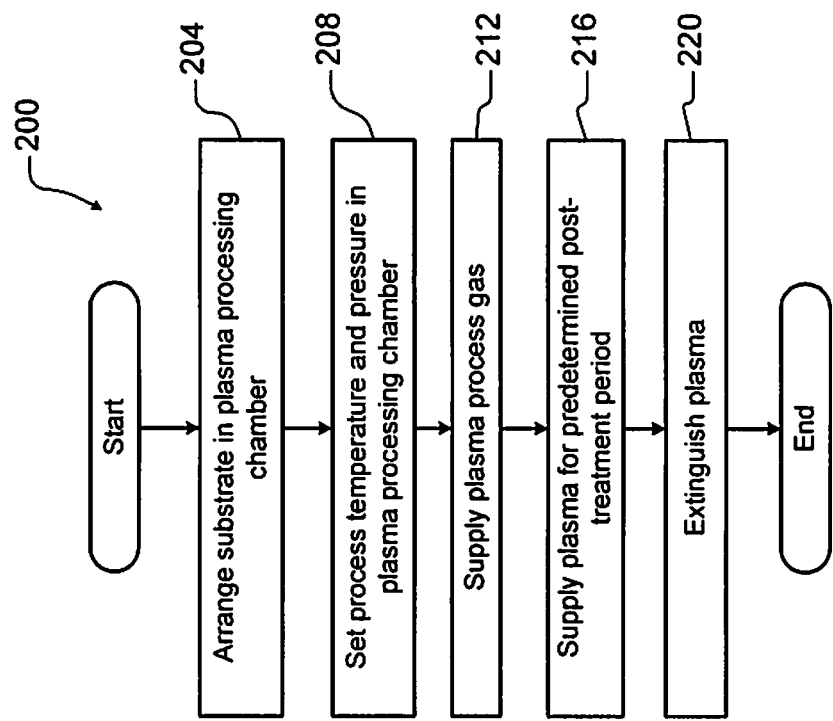
FIG. 6 is a flowchart of an example of a post-treatment method performed after deposition of the barrier layer according to the present disclosure.

Referring now to FIG. 6, a post-treatment method 200 may be performed after depositing the barrier layer. At 204, the substrate is arranged in a plasma processing chamber. In some examples, the plasma processing chamber includes a downstream plasma processing chamber. At 208, process temperature and pressure are set to predetermined values in the plasma processing chamber. At 212, plasma process gas is supplied to the processing chamber. At 216, plasma is struck in the processing chamber for a predetermined post-treatment period. At 220, after the predetermined post-treatment period, the plasma is extinguished.

In some examples, the post-treatment process may employ hydrogen-based plasma, although other plasma process gases may be used. In some examples, the plasma process gas includes forming gas (a mixture of 96% nitrogen and 4% hydrogen gas). In other examples, the plasma process gas includes hydrogen at a concentration between 4% and 100% and molecular nitrogen and/or helium. In some examples, the plasma process gas is either oxygen-free or a small percentage of oxygen (e.g. less than 5%). The amount of oxygen in the plasma process gas can be used to modulate hydrophobic or hydrophilic characteristics that may be used to adjust compatibility of the barrier layer with respect to the photoresist layer.

In some examples, RF power is in a range from 1 kW to 10 kW. In some examples, the RF power is in a range from 4 kW and 5 kW. In some examples, the RF power is approximately 4.5 kW. In some examples, the flow rate of the plasma process gas is in a range from 1 to 20 liters per minute. In some examples, the flow rate is a range from 8 to 12 liters per minute. In some examples, the flow rate of the plasma process gas is 10 liters per minute. In some examples, the process pressure is in a range from 300 mTorr to 5 Torr. In some examples, the process pressure is in a range from 1 Torr to 2 Torr. In some examples, the process pressure is 1.5 Torr. In some examples, the process temperature is in a range from 200 to 400° C.

Figure 7:
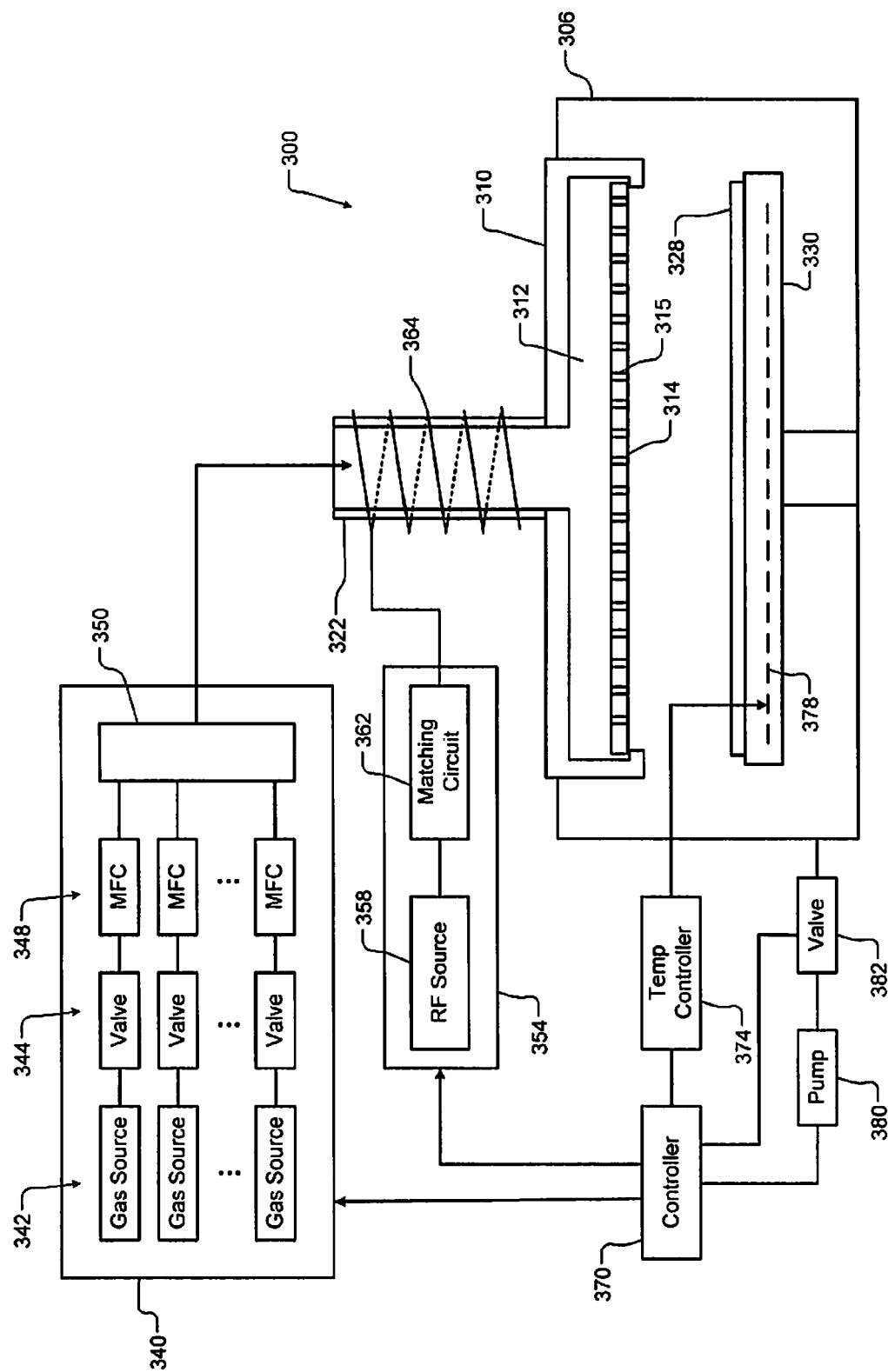
FIG. 7 is a schematic of an example of a substrate processing chamber for pretreatment, deposition of the barrier layer, and/or post-treatment.

Referring now to FIG. 7, an example of a substrate processing chamber 300 for pretreatment, deposition of the barrier layer and/or post-treatment is shown. While a specific processing chamber is shown, other types of processing chambers can be used. The substrate processing chamber 300 includes a chamber 306 and a gas distribution device such as a showerhead 310. The showerhead 310 defines a gas plenum 312 and includes a faceplate 314 including a plurality of distributed through holes. The showerhead 310 distributes process gas substantially uniformly relative to a substrate 328 that is arranged on a substrate support 330 such as a pedestal, electrostatic chuck (ESC) or other substrate support.

A gas delivery system 340 includes one or more gas sources 342, one or more valves 344, one or more mass flow controllers 348 and a manifold 350. The gas delivery system 340 delivers purge gas and process gases to the showerhead 310. An RF generator 354 includes an RF source 358 that supplies RF power during pretreatment and post-treatment processes and a matching circuit 362 that matches an impedance of an inductive coil 364.

A controller 370 is configured to control the gas delivery system 340, the RF generator 354, temperature and pressure. In addition, the controller 370 may include and/or control a temperature controller 374 for controlling the temperature of the substrate support 330 using heaters, fluid channels, thermoelectric devices, etc., which are generally identified at 378. A pump 380 and an optional valve 382 may be used to evacuate reactants from the chamber 306 and/or to control pressure within the chamber 306. In some examples, the pump 380 may be a turbomolecular pump. As can be appreciated, the pretreatment, deposition and post-treatment can be performed in the same processing chamber or in different processing chambers.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules, circuit elements, semiconductor layers, etc.) are described using various terms, including "connected," "engaged," "coupled," "adjacent," "next to," "on top of," "above," "below," and "disposed." Unless explicitly described as being "direct," when a relationship between first and second elements is described in the above disclosure, that relationship can be a direct relationship where no other intervening elements are present between the first and second elements, but can also be an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In some implementations, a controller is part of a system, which may be part of the above-described examples. Such systems can comprise semiconductor processing equipment, including a processing tool or tools, chamber or chambers, a platform or platforms for processing, and/or specific processing components (a wafer pedestal, a gas flow system, etc.). These systems may be integrated with electronics for controlling their operation before, during, and after processing of a semiconductor wafer or substrate. The electronics may be referred to as the "controller," which may control various components or subparts of the system or systems. The controller, depending on the processing requirements and/or the type of system, may be programmed to control any of the processes disclosed herein, including the delivery of processing gases, temperature settings (e.g., heating and/or cooling), pressure settings, vacuum settings, power settings, radio frequency (RF) generator settings, RF matching circuit settings, frequency settings, flow rate settings, fluid delivery settings, positional and operation settings, wafer transfers into and out of a tool and other transfer tools and/or load locks connected to or interfaced with a specific system.

Broadly speaking, the controller may be defined as electronics having various integrated circuits, logic, memory, and/or software that receive instructions, issue instructions, control operation, enable cleaning operations, enable endpoint measurements, and the like. The integrated circuits may include chips in the form of firmware that store program instructions, digital signal processors (DSPs), chips defined as application specific integrated circuits (ASICs), and/or one or more microprocessors, or microcontrollers that execute program instructions (e.g., software). Program instructions may be instructions communicated to the controller in the form of various individual settings (or program files), defining operational parameters for carrying out a particular process on or for a semiconductor wafer or to a system. The operational parameters may, in some embodiments, be part of a recipe defined by process engineers to accomplish one or more processing steps during the fabrication of one or more layers, materials, metals, oxides, silicon, silicon dioxide, surfaces, circuits, and/or dies of a wafer.

The controller, in some implementations, may be a part of or coupled to a computer that is integrated with the system, coupled to the system, otherwise networked to the system, or a combination thereof. For example, the controller may be in the "cloud" or all or a part of a fab host computer system, which can allow for remote access of the wafer processing. The computer may enable remote access to the system to monitor current progress of fabrication operations, examine a history of past fabrication operations, examine trends or performance metrics from a plurality of fabrication operations, to change parameters of current processing, to set processing steps to follow a current processing, or to start a new process. In some examples, a remote computer (e.g. a server) can provide process recipes to a system over a network, which may include a local network or the Internet. The remote computer may include a user interface that enables entry or programming of parameters and/or settings, which are then communicated to the system from the remote computer. In some examples, the controller receives instructions in the form of data, which specify parameters for each of the processing steps to be performed during one or more operations. It should be understood that the parameters may be specific to the type of process to be performed and the type of tool that the controller is configured to interface with or control. Thus as described above, the controller may be distributed, such as by comprising one or more discrete controllers that are networked together and working towards a common purpose, such as the processes and controls described herein. An example of a distributed controller for such purposes would be one or more integrated circuits on a chamber in communication with one or more integrated circuits located remotely (such as at the platform level or as part of a remote computer) that combine to control a process on the chamber.

Without limitation, example systems may include a plasma etch chamber or module, a deposition chamber or module, a spin-rinse chamber or module, a metal plating chamber or module, a clean chamber or module, a bevel edge etch chamber or module, a physical vapor deposition (PVD) chamber or module, a chemical vapor deposition (CVD) chamber or module, an atomic layer deposition (ALD) chamber or module, an atomic layer etch (ALE) chamber or module, an ion implantation chamber or module, a track chamber or module, and any other semiconductor processing systems that may be associated or used in the fabrication and/or manufacturing of semiconductor wafers.

As noted above, depending on the process step or steps to be performed by the tool, the controller might communicate with one or more of other tool circuits or modules, other tool components, cluster tools, other tool interfaces, adjacent tools, neighboring tools, tools located throughout a factory, a main computer, another controller, or tools used in material transport that bring containers of wafers to and from tool locations and/or load ports in a semiconductor manufacturing factory.

What is claimed is:

1. A method for depositing a barrier layer, comprising:
   a) arranging a substrate including a nitride layer in a processing chamber;
   b) setting a process temperature in the processing chamber to a predetermined process temperature range;
   c) setting a process pressure in the processing chamber to a predetermined process pressure range;
   d) supplying at least one of a gas and a vapor including an organosilane precursor species; and
   e) depositing a barrier layer on the nitride layer, wherein the barrier layer is distinct from the nitride layer, wherein the barrier layer reduces diffusion of nitrogen-containing groups in the nitride layer into a photoresist layer that is subsequently deposited on the nitride layer.

2. The method of claim 1, wherein the organosilane species includes one or more $SiCH_3$ functional groups.

3. The method of claim 1, wherein the organosilane species has a form $R_nS_iX_m$, wherein R includes one or more organic functional groups and X includes one or more hydrolysable functional groups that react with —OH or —H active sites on a surface of the substrate.

4. The method of claim 3, wherein the one or more hydrolysable functional groups are selected from a group consisting of primary amine groups, secondary amine groups, tertiary amine groups, alcoxy groups (—OR), acyloxy groups (—O(CO)R), and halogen atoms.

5. The method of claim 1, further comprising performing plasma pretreatment on the nitride layer before e).

6. The method of claim 1, further comprising performing plasma post-treatment on the barrier layer after e).

7. The method of claim 1, further comprising:
   f) depositing a photoresist layer on the barrier layer.

8. The method of claim 7, further comprising performing a plasma post-treatment process on the barrier layer after e) and before f).

9. The method of claim 1, wherein the organosilane species bond with SiOH and SiH dangling bonds.

10. The method of claim 1, wherein the organosilane species is selected from a group consisting of dimethylaminotrimethylsilane (DMATMS), Di(sec-butylamino)silane (DSBAS), and bis(tert-butylamino)silane (BTBAS).

11. The method of claim 1, wherein the predetermined process temperature range is from 200° C. to 400° C.

12. The method of claim 1, wherein the predetermined process temperature range is from 260° C. to 300° C.

13. The method of claim 1, wherein the predetermined process pressure range is from 300 mTorr to 5 Torr.

14. The method of claim 1, wherein the predetermined process pressure range is from 1 Torr to 2 Torr.

15. The method of claim 1, wherein the barrier layer has a thickness of 5 Å to 100 Å.

16. The method of claim 1, wherein the barrier layer has a thickness of 10 Å to 20 Å.

17. The method of claim 1, wherein d) further comprises supplying a carrier gas selected from a group consisting of molecular hydrogen, molecular nitrogen, argon, helium, and an inert gas.

18. The method of claim 1, wherein the nitride layer is selected from a group consisting of silicon nitride and silicon carbonitride.

19. The method of claim 5, wherein performing the plasma pretreatment includes exposing the nitride layer to plasma process gas including hydrogen.

20. The method of claim 19, wherein the hydrogen comprises 4% to 100% of the plasma process gas.

* * * * *